(12) United States Patent
Baars et al.

(10) Patent No.: US 10,088,405 B2
(45) Date of Patent: Oct. 2, 2018

(54) METHOD FOR OPERATING A PARTICLE SENSOR

(71) Applicant: Robert Bosch GmbH, Stuttgart (DE)

(72) Inventors: Enno Baars, Leonberg (DE); Andy Tiefenbach, Vaihingen-Horrheim (DE); Michael Bessen, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 67 days.

(21) Appl. No.: 15/314,738

(22) PCT Filed: May 29, 2015

(86) PCT No.: PCT/EP2015/061952
§ 371 (c)(1),
(2) Date: Nov. 29, 2016

(87) PCT Pub. No.: WO2015/193079
PCT Pub. Date: Dec. 23, 2015

(65) Prior Publication Data
US 2017/0199111 A1 Jul. 13, 2017

(30) Foreign Application Priority Data
Jun. 17, 2014 (DE) .................... 10 2014 211 533

(51) Int. Cl.
*G01N 15/06* (2006.01)
*F01N 11/00* (2006.01)
(Continued)

(52) U.S. Cl.
CPC ....... *G01N 15/0656* (2013.01); *F01N 11/002* (2013.01); *F01N 11/007* (2013.01);
(Continued)

(58) Field of Classification Search
CPC ......... G01N 15/0656; G01N 35/00613; G01N 35/00712; F01N 2560/05; F01N 2560/20;
(Continued)

(56) References Cited

U.S. PATENT DOCUMENTS 7,609,068 B2* 10/2009 Ripley ............... G01N 15/0656
324/500
8,015,862 B2* 9/2011 Bollinger ........... G01N 15/0656
73/114.69
(Continued)

FOREIGN PATENT DOCUMENTS

DE 102006009066 A1 10/2006
DE 102008031648 A1 1/2010
(Continued)

OTHER PUBLICATIONS

International Search Report dated Sep. 2, 2015, issued in the corresponding International Patent Application PCT/EP2015/061952 filed May 29, 2015.

*Primary Examiner* — Freddie Kirkland, III
(74) *Attorney, Agent, or Firm* — Norton Rose Fulbright US LLP; Gerard Messina

(57) ABSTRACT

A method for determining soot in exhaust gases of burners or internal combustion engines with the aid of a sensor element which includes at least two measuring electrodes exposed to the exhaust gas and one heating element, a voltage being applied to the at least two measuring electrodes during a measuring phase and the current flow or electrical resistance occurring between the measuring electrodes being determined and output as a measure for the particle concentration or the particle mass flow, characterized in that during the measuring phase, the temperature of the sensor element is monitored and the sensor element is
(Continued)

heated by the heating element, if the temperature of the sensor element falls below a limiting temperature.

12 Claims, 4 Drawing Sheets

(51) Int. Cl.
    *F02D 41/04*     (2006.01)
    *F02D 41/14*     (2006.01)
    *G01M 15/10*     (2006.01)

(52) U.S. Cl.
    CPC ....... *F02D 41/042* (2013.01); *F02D 41/1466* (2013.01); *F02D 41/1494* (2013.01); *G01M 15/102* (2013.01); *F01N 2560/05* (2013.01); *F01N 2560/06* (2013.01); *F01N 2560/12* (2013.01); *F01N 2560/20* (2013.01); *Y02T 10/47* (2013.01)

(58) Field of Classification Search
    CPC ...... F01N 11/00; F01N 2550/04; F01N 9/002; F01N 11/007; F01N 2560/06; F02D 41/1466; F02D 41/1494; G01M 15/102
    See application file for complete search history.

(56) References Cited

U.S. PATENT DOCUMENTS

| | | | |
|---|---|---|---|
| 8,823,400 B2* | 9/2014 | Hocken | F02D 41/1466 |
| | | | 324/691 |
| 9,021,868 B2* | 5/2015 | Sakamoto | F01N 11/00 |
| | | | 73/61.71 |
| 9,151,204 B2* | 10/2015 | Hashida | F01N 11/00 |
| 2009/0090622 A1 | 4/2009 | Ripley | |
| 2010/0031733 A1* | 2/2010 | Bollinger | F02D 41/1466 |
| | | | 73/28.04 |
| 2012/0260636 A1 | 10/2012 | Hashida et al. | |
| 2013/0002271 A1* | 1/2013 | Hocken | F02D 41/1466 |
| | | | 324/705 |
| 2013/0318948 A1* | 12/2013 | Van Marion | F02D 41/1466 |
| | | | 60/277 |

FOREIGN PATENT DOCUMENTS

| | | |
|---|---|---|
| DE | 102012205584 A1 | 10/2013 |
| EP | 2202509 A1 | 6/2010 |

* cited by examiner

METHOD FOR OPERATING A PARTICLE SENSOR

BACKGROUND INFORMATION

In order to check or monitor the functionality of exhaust gas aftertreatment systems used presently in motor vehicles, sensors are needed which make it possible to precisely ascertain the particle concentration present in a combustion exhaust gas. Furthermore, with the aid of such sensors, it should be possible to make a loading prognosis of, for example, a diesel particle filter provided in an exhaust gas system in order to achieve a high system reliability and thus be able to use more cost-effective filter materials.

A sensor for detecting particles in a fluid flow, which is designed based on a ceramic multilayer substrate is described in German Patent Application No. DE 10 2006 009 066. It includes two measuring electrodes spaced apart from one another, which are exposed to the combustion exhaust gas to be tested. If soot is deposited between the two measuring electrodes, a current flow occurs between the measuring electrodes when a direct voltage is applied to the measuring electrodes. A heating element of a layered design makes it possible to remove deposited soot particles from the electrodes or their surroundings thermally by burn-off and regenerate the sensor in this way.

After a successful regeneration, the next measuring phase is provided, in which soot is again deposited between the measuring electrodes.

If the temperature of the sensor element falls below a limiting temperature, for example, 100° C., during the measuring phase, water vapor may condense on the sensor element. Generally, the condensate adhering on and between the measuring electrodes renders the ongoing measurement unusable, making it necessary to interrupt this measuring phase. The sensor element must then first be regenerated by resetting it into the original state. Only after that may a new measuring phase begin.

This reduces the availability of the particle sensor signal pro rata temporis.

SUMMARY

In contrast, the features of the present invention have the effect that measuring phases do not need to be interrupted, but instead may be continued.

According to the present invention, it is provided that during the measuring phase, the temperature of the sensor element is monitored and the sensor element is heated by the heating element if the temperature of the sensor element falls below a limiting temperature.

In this case, the limiting temperature is preferably a temperature which lies below the burn-off temperature of soot. The limiting temperature may lie, for example, in the range of 50° C. through 200° C. Preferably, it lies in the range from 80° C. through 150° C.

It is preferred that the heating of the sensor element by the heating element during the measuring phase occurs only using low heating power, for example, using no more than 2 W or, for example, using no more than 10% of the maximum heating power of the heating element or the maximally occurring heating power of the heating element during operation of the sensor element.

It is preferred that during the heating of the sensor element by the heating element, the limiting temperature is exceeded only slightly at the most, in particular by 50 K at the most.

In a favorable manner, the temperature of the sensor element may be monitored with the aid of a temperature measuring element, which is integrated into the sensor element.

The measuring phases explained above are different from an optionally provided regeneration phase, in which the sensor element may be heated by the heating element to a temperature which is above the burn-off temperature of soot and consequently also above the limiting temperature. For example, this temperature may amount to 600° C. or higher.

The method according to the present invention is in particular advantageous for internal combustion engines which are part of a hybrid drive of a vehicle, or are operated in combination with a start-stop system, since in these cases, states occur in the exhaust gas particularly frequently in which a critical cooling of the sensor element may occur.

A hybrid drive is in particular understood to be a drive which includes an internal combustion engine for driving a vehicle and further an electric motor by which the vehicle may be driven when decoupled from the internal combustion engine. A start-stop system is in particular understood to be a combustion-engine drive for a vehicle, in which it is provided that under certain operating conditions of the internal combustion engine or of the vehicle, for example, idling of the internal combustion engine and/or standstill of the vehicle, the engine is automatically stopped. In particular, an engine start after an engine stop may be triggered in a simplified way from the point of view of the operator, for example, by pressing on a pedal or the like.

It is characteristic of these systems that a corresponding control of the combustion-engine operation is frequently interrupted. It is problematic in this context that no warm combustion exhaust gas is generated in the phases of interrupted combustion-engine operation, and consequently the sensor element situated in the exhaust tract may increasingly be cooled to below the limiting temperature.

The method according to the present invention continuously prevents the sensor element from being cooled insofar as that it is not necessary to interrupt ongoing measuring phases.

An object of the present invention is also a computer program which is designed for carrying out each step of the method and an electronic storage medium on which this computer program is stored and an electronic control unit including such an electronic storage medium.

DETAILED DESCRIPTION OF EXAMPLE EMBODIMENTS

Figure 1:
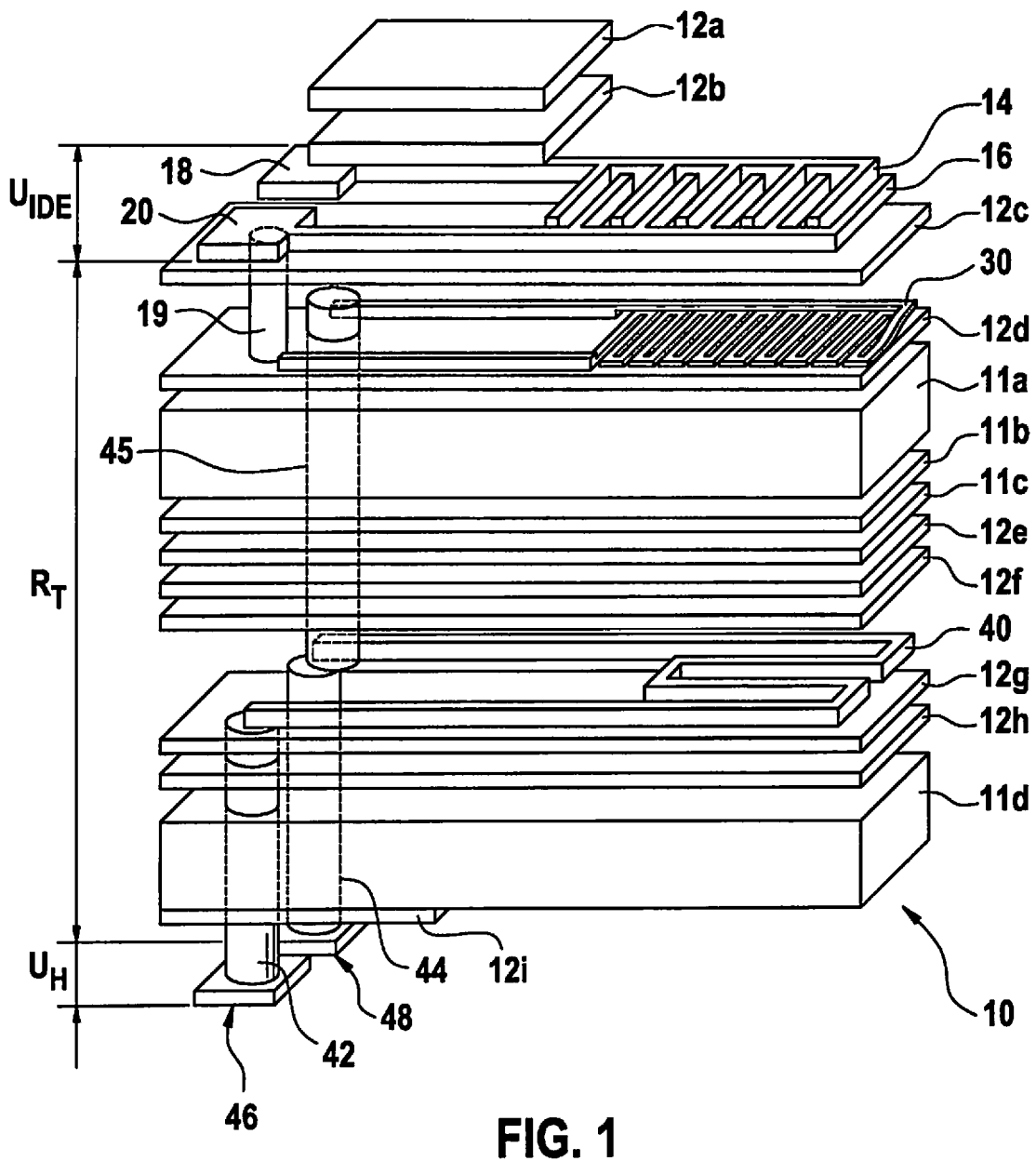
FIG. 1 shows a sensor element according to the related art.

FIG. 1 shows a design of a conventional sensor element of a particle sensor. Denoted as reference numeral 10 is a ceramic sensor element, which is used for determining particles such as, for example, soot particles, in a gas mixture surrounding sensor element 10. Sensor element 10 includes, for example, a plurality of oxygen ion-conducting solid electrolyte layers 11a, 11b, 11c, and 11d. Solid electrolyte layers 11a and 11d are designed as ceramic films and form a planar ceramic body. They are preferably made of an oxygen ion-conducting solid electrolyte material such as, for example, $ZrO_2$ stabilized or partially stabilized using $Y_2O_3$.

In contrast, solid electrolyte layers 11b and 11c are generated by screen-printing a paste-like ceramic material, for example, on solid electrolyte layer 11a. Preferably, the same solid electrolyte material, from which solid electrolyte layers 11a, 11d are also made, is used as a ceramic component of the paste-like material.

Furthermore, sensor element 10 includes, for example, a plurality of electrically insulating ceramic layers 12a, 12b, 12c, 12d, 12e, 12f, 12g, 12h, and 12i. Layers 12a through 12i are also generated by screen-printing a paste-like ceramic material, for example, on solid electrolyte layers 11a, 11c, 11d. For example, barium-containing aluminum oxide is used as a ceramic component of the paste-like material, since it has a largely constantly high electrical resistance over a long period of time even under alternating thermal loads. Alternatively, the use of cerium oxide or the addition of other alkaline earth oxides is also possible.

The integrated form of the planar ceramic body of sensor element 10 is produced by laminating together the ceramic films printed with solid electrolyte layers 11b, 11c and including functional layers as well as layers 12a-12i and subsequently sintering the laminated structure in a manner known per se.

Sensor element 10 furthermore includes a ceramic heating element 40, which is designed in the form of an electrical resistance conductor track, and is used for heating sensor element 10 in particular to the temperature of the gas mixture to be determined or for burning off the soot particles deposited on the large surfaces of sensor element 10. The resistance conductor track is preferably designed from a cermet material; preferably as a mixture of platinum or a platinum metal including ceramic fractions such as, for example, aluminum oxide. The resistance conductor track is furthermore preferably designed in the shape of a meander and has vias 42, 44 as well as electrical contacts 46, 48 at both ends. The application of an appropriate heating voltage $U_H$ to contacts 46, 48 of the resistance conductor track makes it possible to regulate the heating power of heating element 40 accordingly.

For example, two measuring electrodes are attached on a large surface of sensor element 10, the measuring electrodes preferably being designed as interdigital electrodes which are intermeshed with one another and form a measuring element. The use of interdigital electrodes as measuring electrodes advantageously makes it possible to determine the electrical resistance or the electrical conductance of the surface material located between the measuring electrodes in a particularly precise manner. For contacting the measuring electrodes, contacts 18, 20 are provided in the area of an end of the sensor element facing away from the gas mixture. The supply areas of the electrodes are preferably shielded from the influences of a gas mixture surrounding sensor element 10 by electrically insulating layers 12a, 12b.

On the large surface of sensor element 10 provided with the measuring electrodes, a porous cover or protective layer may be additionally provided which is not shown for reasons of clarity and which shields the measuring electrodes in the area in which they are intermeshed from being in direct contact with the gas mixture to be determined. The layer thickness of the porous protective layer is preferably greater than the layer thickness of the measuring electrodes. The porous protective layer is preferably of an open-pore design, the pore size being selected in such a way that the particles to be determined in the gas mixture may diffuse into the pores of the porous protective layer. The pore size of the porous protective layer preferably lies in a range of 2 μm through 10 μm. The porous protective layer is made of a ceramic material, which is preferably similar to the material of layer 12a or identical to it and may be produced using screen-printing. The porosity of the porous protective layer may be set appropriately by adding pore generators to the screen printing paste.

A voltage $U_{IDE}$ is applied to the measuring electrodes during the operation of sensor element 10. Since the measuring electrodes are situated on the surface of electrically insulating layer 12c, there is at first essentially no current flow between the measuring electrodes.

If a gas mixture flowing around sensor element 10 contains particles, in particular soot, they are deposited on the surface of sensor element 10. Since soot has a certain electrical conductivity, if there is an adequate loading of soot on the surface of sensor element 10 or of the porous protective layer, an increasing current flow $U_{IDE}$ occurs between the measuring electrodes, which is correlated with the extent of the loading.

If a direct voltage $U_{IDE}$ is now applied to the measuring electrodes and the current flow occurring between the measuring electrodes is ascertained, it is thus possible to infer from the current flow the deposited particle mass or the instantaneous particle mass flow, in particular soot mass flow, and the particle concentration in the gas mixture. This measuring method is used for detecting the concentration of all the particles in a gas mixture which influence the electrical conductivity of the ceramic material located between the measuring electrodes positively or negatively.

Another possibility is to ascertain the increase in the current flow over time and to infer from the quotient of the current flow increase and time or from the differential quotient of the current flow after time, the deposited particle mass or the instantaneous particle mass flow, in particular soot mass flow, and the particle concentration in the gas mixture. A calculation of the particle concentration is possible based on the measured values, provided the flow speed of the gas mixture is known. This flow speed or the volume flow of the gas mixture may, for example, be determined with the aid of a suitable additional sensor.

Furthermore, sensor element 10 includes a temperature measuring element 30, which is preferably designed in the form of an electrical resistance conductor track. The resistance conductor track is, for example, made of a similar or the same material as the resistance conductor track of heating element 40. The resistance conductor track of temperature measuring element 30 is preferably designed in the form of a meander, one of the terminals of the resistance conductor track preferably being connected to contact 48 by a via 45. Another electrical terminal of temperature measuring element 30 is preferably conductively connected to one of contacts 18, 20 by another via 19. By applying an appropriate voltage to terminals 20, 48 of the resistance conductor track and by determining electrical resistance $R_T$ of the same, the temperature of sensor element 10 may be inferred. Alternatively, a temperature determination using thermocouples is possible. A further alternative or additional possibility of the temperature measurement is to determine the temperature-dependent conductivity of the ceramic body situated between the resistance conductor track of temperature measuring element 30 and the measuring electrodes and to infer from its level the temperature of the sensor element.

Figure 2:
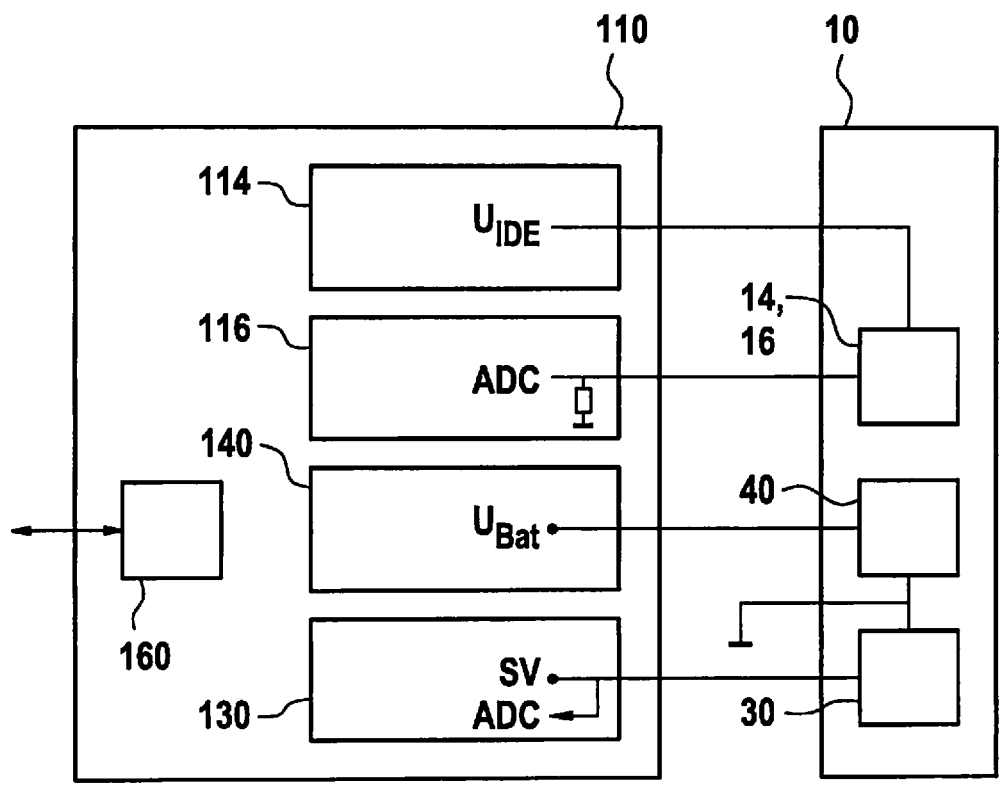
FIG. 2 shows a block diagram of an exemplary circuit of the sensor element.

FIG. 2 shows a possible circuit 110 for sensor element 10 as a block diagram. Circuit 110 may be integrated, for example, in a plug connector of the particle sensor.

Accordingly, temperature measuring element 30 is connected to a temperature measuring unit 130 of circuit 110 and is connected between a ground potential and a supply voltage of 5 V. Corresponding to the electrical resistance of temperature measuring element 30, it is possible to infer the temperature of sensor element 10 from the resulting current flow.

Heating element 40 is connected to a heating unit 140 of circuit 110 and is connected between a ground potential and a battery voltage of 12 V. The effective heating power generated by heating element 40 may, for example, be adjusted using pulse width modulation.

A measuring voltage $U_{IDE}$ of, for example, 46 V is applied between measuring electrodes 14, 16. Corresponding to the electrical resistance between measuring electrodes 14, 16, it is possible to infer a particle accumulation in the area between measuring electrodes 14, 16 from the resulting current flow.

Part of the circuit is also a communication unit 160 for communicating with an engine control unit, which is designed, for example, as a CAN interface.

Figure 3:
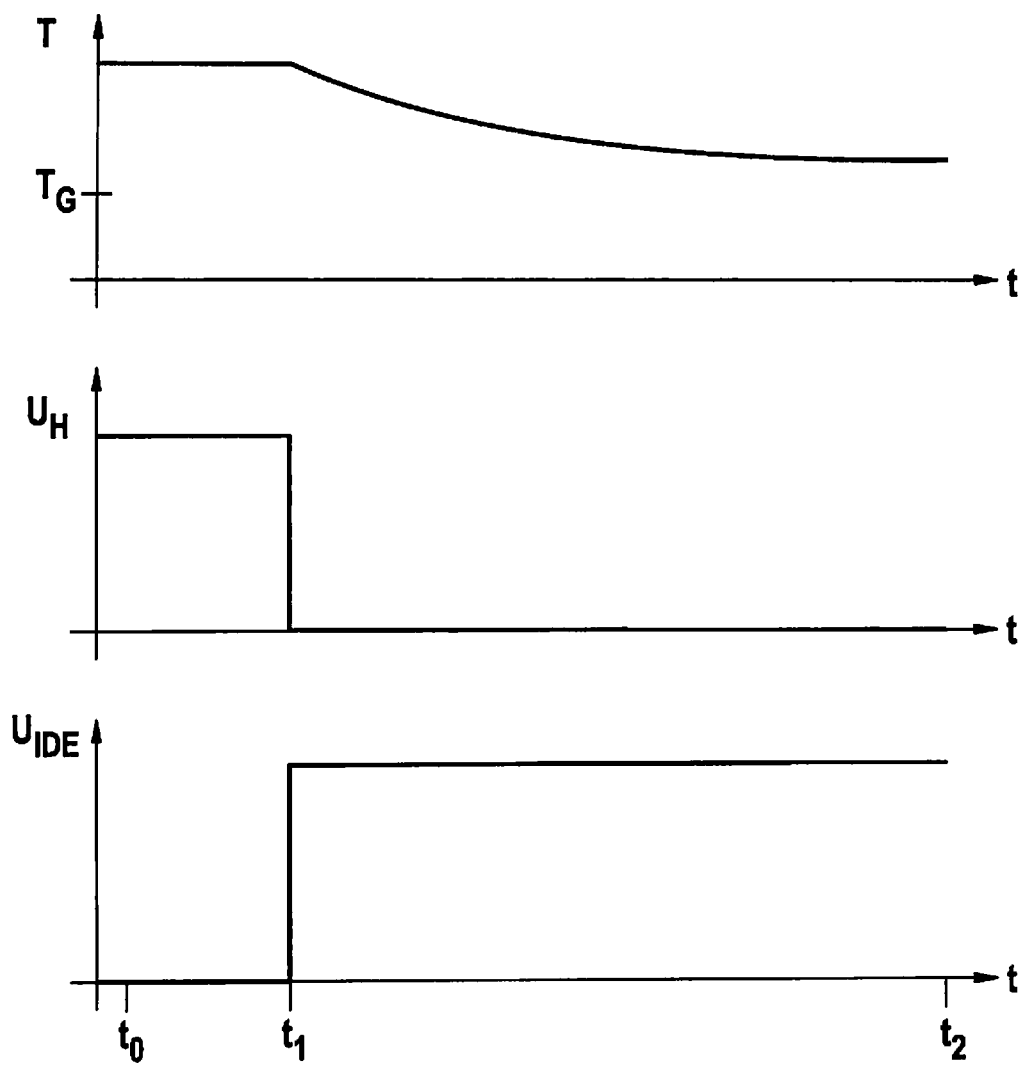
FIG. 3 shows a sequence of the method according to the present invention in an uncritical situation.

FIG. 3 shows a sequence of the method according to the present invention in an uncritical situation, which, for example, corresponds to a situation in which sensor element 10 is continuously acted upon by hot exhaust gas.

In the upper part of FIG. 3, temperature T of sensor element 10 is shown, as it may be ascertained, for example, using temperature measuring unit 130. In the center part of FIG. 3, the effective value of voltage $U_H$ applied to heating element 40 is shown. In the lower part of FIG. 3, measuring voltage $U_{IDE}$ is shown.

During a first regeneration phase, in the time period between t0 and t1, measuring voltage $U_{IDE}$ applied between measuring electrodes 14, 16 is 0 V; the effective value of voltage $U_H$ applied to heating element 40 has a high, in particular a maximum value, for example, 12 V; accordingly, temperature T of sensor element 10 is also high, for example, 600° C.

At point in time t1, the first regeneration phase ends and a first measuring phase follows. For this purpose, a measuring voltage $U_{IDE}$ of 46 V is applied between measuring electrodes 14, 16 and heating element 40 is deactivated (0 V).

Consistent with the deactivated heating, temperature T of sensor element 10 drops, but it remains above limiting temperature $T_G$, i.e., in an uncritical range, until the end of the measuring phase at point in time t2. Activation of heating element 40 during the measuring phase is thus not necessary in this example.

Figure 4:
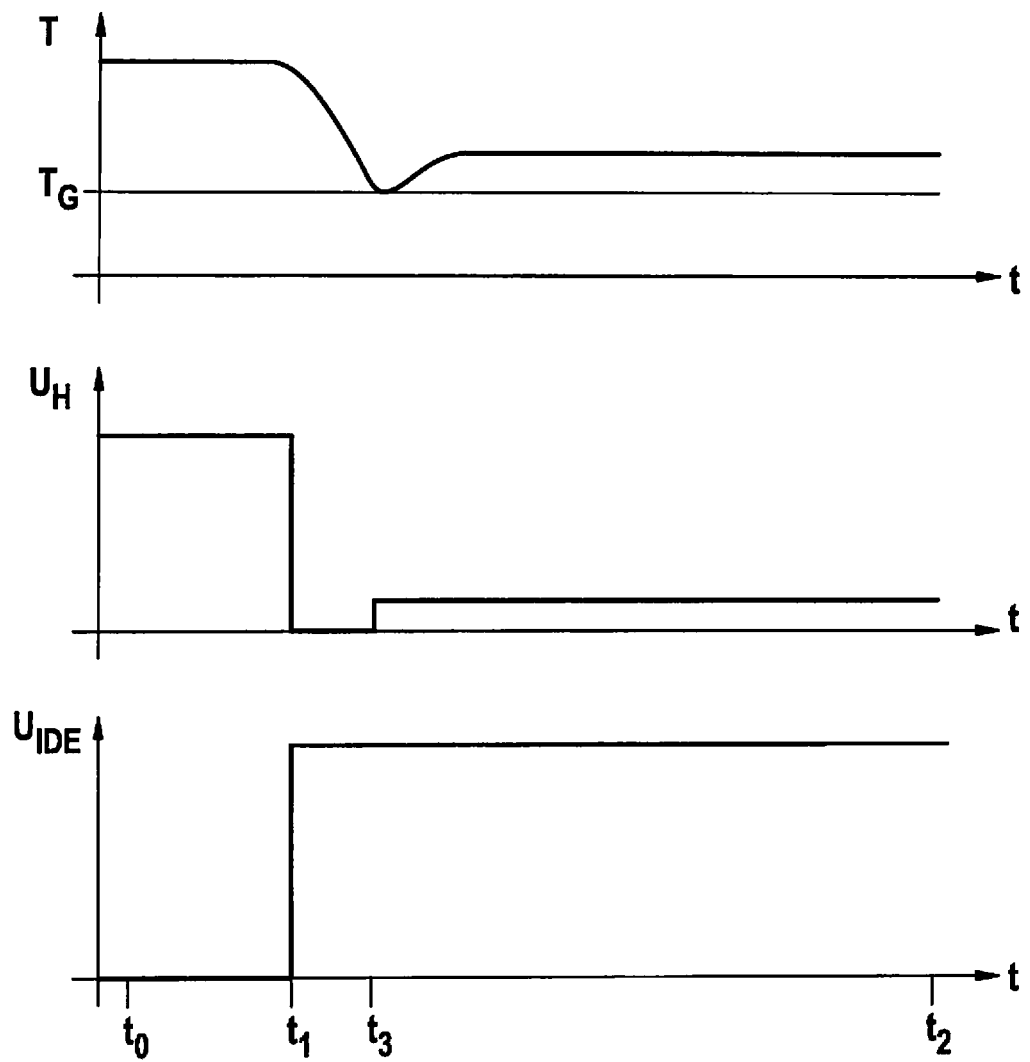
FIG. 4 shows a sequence of the method according to the present invention when the sensor element is cooled to under a limiting temperature.

FIG. 4 shows a sequence of the method according to the present invention in a situation in which the danger of cooling of sensor element 10 is present. This is the case, for example, during electric operation in a hybrid vehicle and in stop phases in start-stop systems.

In contrast to the sequence shown in FIG. 3, temperature T of sensor element 10 reaches or falls below limiting temperature $T_G$, which is, for example, 100° C., at point in time t3 during the first measuring phase. In response to this cooling, heating element 40 is activated in that temperature T of sensor element 10 rises somewhat, for example, to 120° C., and remains at this value for the remainder of the first measuring phase. The effective value of heating voltage $U_H$ is here, for example, 2.5 V.

What is claimed is:

1. A method for determining soot in exhaust gases of a burner or internal combustion engine with the aid of a sensor element which includes at least two measuring electrodes exposed to the exhaust gas and one heating element, the method comprising:
    applying a voltage to the at least two measuring electrodes during a measuring phase;
    determining a current flow or electrical resistance occurring between the measuring electrodes;
    outputting the determined current flow or electrical resistance as a measure for a particle concentration or a particle mass flow; and
    during the measuring phase, while applying the voltage, monitoring a temperature of the sensor element and heating the sensor element using the heating element if the temperature of the sensor element falls below a limiting temperature.

2. The method as recited in claim 1, wherein the limiting temperature is a temperature which lies below a burn-off temperature of soot.

3. The method as recited in claim 1, wherein the limiting temperature is in a range of 50° C. through 200° C.

4. The method as recited in claim 1, wherein the limiting temperature is in a range of 80° C. through 150° C.

5. The method as recited in claim 1, wherein when the sensor element is heated by the heating element, the limiting temperature is exceeded by 50 K at the most.

6. The method as recited in claim 1, wherein the sensor element includes a temperature measuring element, and the temperature of the sensor element is monitored with the aid of the temperature measuring element.

7. The method as recited in claim 1, wherein regeneration phases are provided, in which the sensor element is heated by the heating element to a temperature which lies above a burn-off temperature of soot, the burn-off temperature being above 600° C.

8. The method as recited in claim 1, wherein the internal combustion engine is part of a hybrid drive of a vehicle and the temperature of the sensor element falls below the limiting temperature while the vehicle is driven electrically and the internal combustion engine is deactivated.

9. The method as recited in claim 1, wherein the internal combustion engine is part of a vehicle having a start-stop system and the temperature of the sensor element falls below the limiting temperature during a stop phase.

10. The method as recited in claim 1, wherein the internal combustion engine is assigned an exhaust tract in which the sensor element is situated and through which an exhaust gas flows at least temporarily, the temperature of which is lower than the limiting temperature.

11. A non-transitory electronic storage medium on which is stored a computer program for determining soot in exhaust gases of a burner or internal combustion engine with the aid of a sensor element which includes at least two measuring electrodes exposed to the exhaust gas and one heating element, the computer program, when executed by a processor, causing the processor to perform:
    applying a voltage to the at least two measuring electrodes during a measuring phase;
    determining a current flow or electrical resistance occurring between the measuring electrodes;
    outputting the determined current flow or electrical resistance as a measure for a particle concentration or a particle mass flow; and
    during the measuring phase, while applying the voltage, monitoring a temperature of the sensor element and heating the sensor element using the heating element if the temperature of the sensor element falls below a limiting temperature.

12. An electronic control unit which includes a non-transitory electronic storage medium on which is stored a computer program for determining soot in exhaust gases of a burner or internal combustion engine with the aid of a sensor element which includes at least two measuring electrodes exposed to the exhaust gas and one heating element, the computer program, when executed by the electronic control unit, causing the electronic control unit to perform:
    applying a voltage to the at least two measuring electrodes during a measuring phase;
    determining a current flow or electrical resistance occurring between the measuring electrodes;
    outputting the determined current flow or electrical resistance as a measure for a particle concentration or a particle mass flow; and
    during the measuring phase, while applying the voltage, monitoring a temperature of the sensor element and heating the sensor element using the heating element if the temperature of the sensor element falls below a limiting temperature.

\* \* \* \* \*